United States Patent [19]

Marino

[11] Patent Number: 4,751,923

[45] Date of Patent: Jun. 21, 1988

[54] SLING, SHOULDER IMMOBILIZER AND POSTURE CORRECTOR

[76] Inventor: Michael P. Marino, 1538 Cinnamond St., Napa, Calif. 94559

[21] Appl. No.: 56,807

[22] Filed: Jun. 2, 1987

[51] Int. Cl.$^4$ ............................................. A61F 5/40
[52] U.S. Cl. ..................................... 128/94; 128/133; 128/134; 224/901; 224/206
[58] Field of Search ................. 128/94, 154, 155, 170, 128/171, 133, 134, 135

[56] References Cited

U.S. PATENT DOCUMENTS

| | | | |
|---|---|---|---|
| 114,615 | 5/1871 | Smitley | 128/94 |
| 686,338 | 11/1901 | Ready | 128/133 |
| 1,123,278 | 1/1915 | Hallett | 128/134 |
| 1,697,363 | 1/1929 | Losey | 128/134 |
| 3,780,729 | 12/1973 | Garnett | 128/94 |
| 4,396,013 | 8/1983 | Hasslinger | 128/133 |

FOREIGN PATENT DOCUMENTS 5482 10/1905 France ................................. 128/78

Primary Examiner—Richard J. Johnson
Assistant Examiner—Charles H. Sam
Attorney, Agent, or Firm—Melvin R. Stidham

[57] ABSTRACT

The disclosure is of an arm brace comprising a chest strap which is extended around the chest and fastened snugly in place by means of a Velcro type fastener. A shoulder strap extends over the shoulder from a selected position in back to a selected position in front and extended through a belt loop and secured in place by complementary fastener components. A wrist strap is supported by the shoulder strap and is wrapped around the wrist and adjustably fastened. The shoulder may be completely or partially immobilized by attaching the upper arm to the chest strap at the side, wrapped around the arm and fastened. The forearm may be secured to the chest strap and supported similarly to the wrist support.

21 Claims, 3 Drawing Sheets

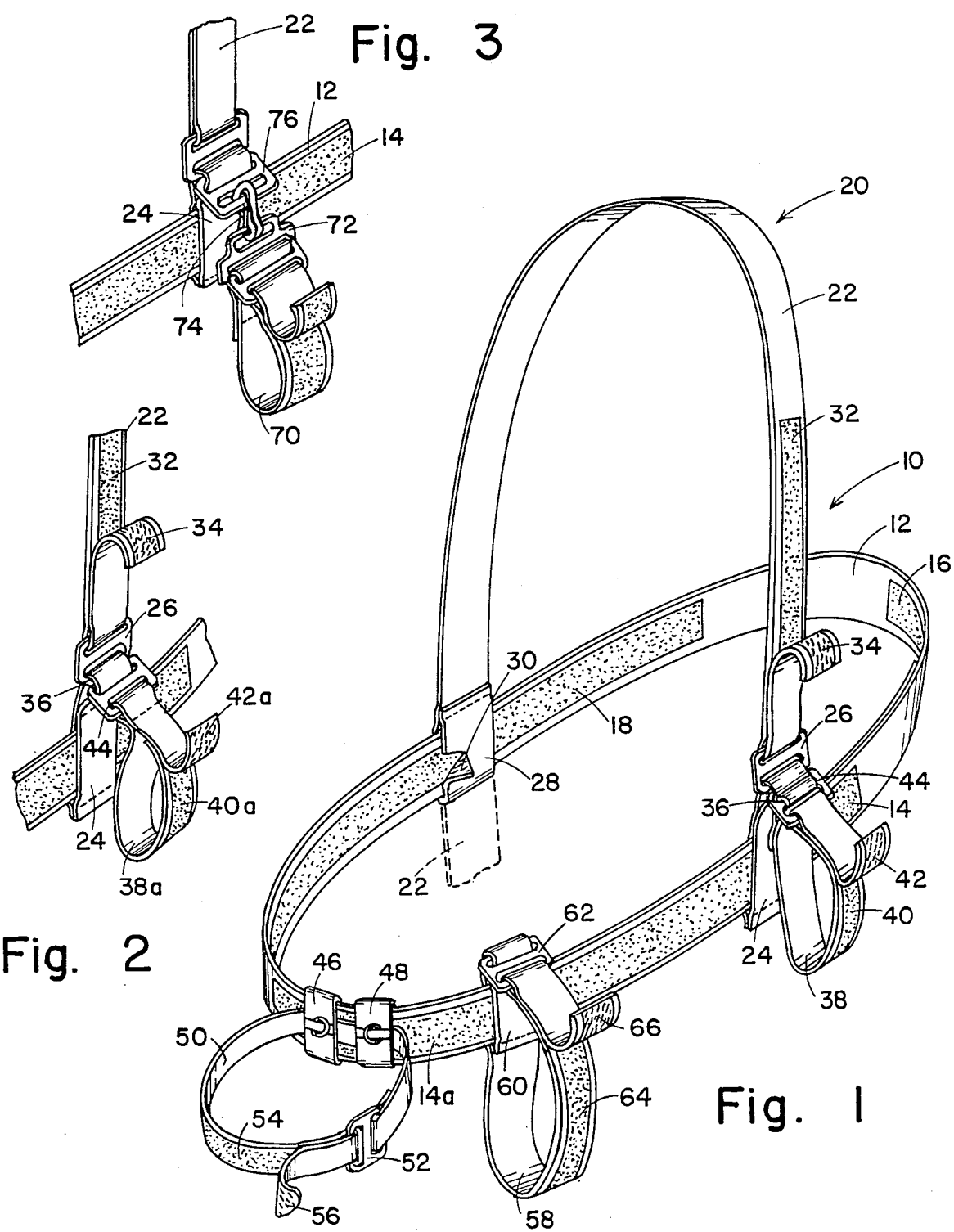

SLING, SHOULDER IMMOBILIZER AND POSTURE CORRECTOR

BACKGROUND OF THE INVENTION

This invention relates to a surgical appliance for selectively immobilizing a shoulder, for serving as a sling for restricting the range of motion of the affected arm, or for correcting the posture of certain patients, such as stroke victims. A form of shoulder immobilizer currently in use includes a wide elastic bandage that is wrapped around the upper body and carries wrist and arm straps to hold the arm firmly against the side. A shoulder strap is provided to prevent the unit from sliding down on the body. In use, it has been found that the elastic bandage, when tightly applied, applies an excessive amount of constricting pressure on the muscles in the small of the back, as well as to the ribs. As a result, some wearers have experienced major back pain and suffered from soreness of the ribs. In addition, the shoulder strap, being of triangular configuration cuts into the back of the neck. Another disadvantage of many prior shoulder immobilizers and slings resides in the fact that they cannot be applied by the patient without assistance.

Lilla U.S. Pat. No. 4,497,316 shows a sling, which is conditioned to suspend the arm at various levels. However, it is limited in function to suspension of the forearm.

Honneffer U.S. Pat. No. 4,198,964 and Augustyniak U.S. Pat. No. 4,188,944 show appliances for immobilizing the upper arm and shoulder while applying a downward force to the acromio-clavicular joint.

OBJECTS OF THE INVENTION

It is an object of this invention to provide a medical appliance that holds the arm and shoulder in comfortable and natural positions. It is a further object of this invention to provide an arm and shoulder holder that can be worn without tightly constricting the body to provide internal pressures to the stomach, ribs and back muscles.

It is a further object of this invention to provide an appliance that can effectively immobilize the shoulder and suspend the lower arm.

It is a further object of this invention to provide an appliance that can be adjusted by the patient to suspend an immobile arm at adjusted elevation.

It is a further object of this invention to provide an appliance that can be adjusted to provide various limited ranges of motion to the upper arm or to immobilize the upper arm and shoulder completely.

It is a further object of this invention to provide an arm and shoulder holder that can be put on and taken off by the patient without assistance.

It is a further object of this invention to provide an appliance that will correct the posture of certain patients, such as stroke victims.

Other objects and advantages of this invention will become apparent from the description to follow, particularly when read in conjunction with the accompanying drawing.

SUMMARY OF THE INVENTION

In carrying out this invention, a chest strap is provided as the basic anchoring member. A shoulder strap is provided to extend from any one of a range of positions in the back and extend over the shoulder to buckle to a fixed adjustable position in the front. A wrist strap is suspended from the shoulder strap and, some embodiments can be applied by the patient without assistance. An arm restraint strap is fixed to a side of the chest strap and is wrapped around the upper arm of the wearer. It can be adjusted to immobilize the shoulder completely, to allow only slight movement of the upper arm or to enable a limited range of movement of the arm away from the side.

BRIEF DESCRIPTION OF THE DRAWINGS

In the drawings:

FIG. 1 is a view in perspective of the sling and shoulder immobilizer of this invention;

FIG. 2 is a partial view in perspective showing another form of wrist strap;

FIG. 3 is a partial view in perspective showing still another form of wrist strap;

DESCRIPTION OF A PREFERRED EMBODIMENT

Figure 5:
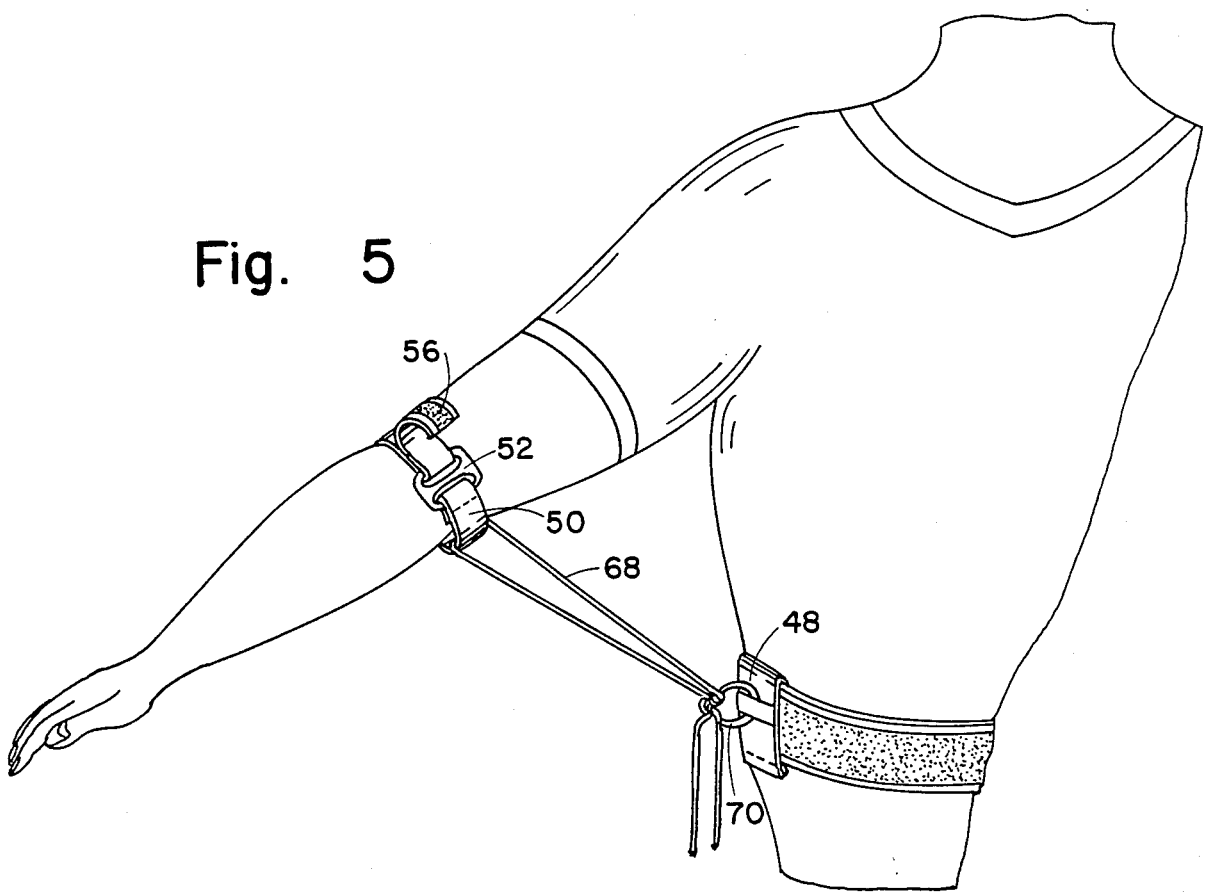
FIG. 5 is a view in perspective showing a chest strap accessory for enabling a limited range of arm movement.
Figure 4:
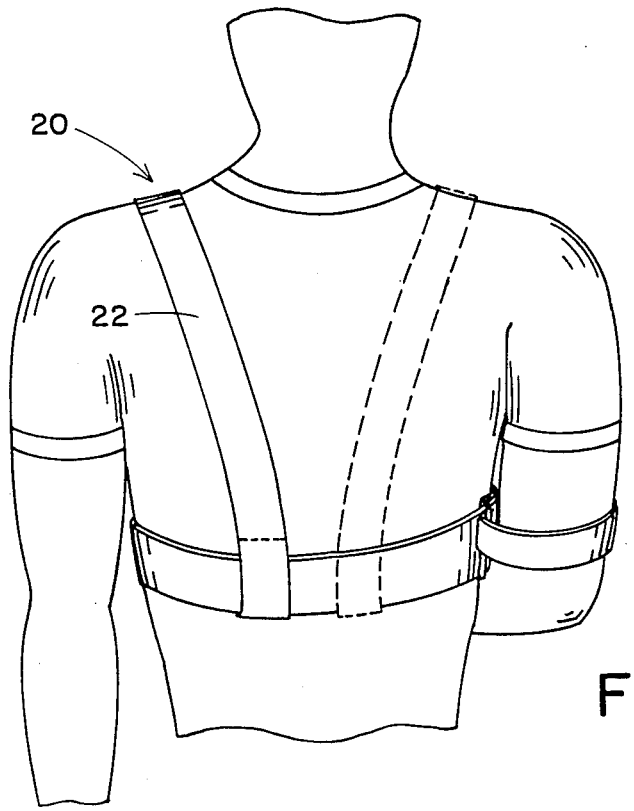
FIG. 4 is a view in perspective showing the attachment and adjustment of the shoulder strap to the chest strap.

Referring now to the drawings in greater detail, and particularly to FIG. 1, the surgical appliance 10 of this invention includes as its basic anchoring component a chest strap 12. The chest strap 12 is applied to encircle the upper body of the wearer and applied snugly, but not tightly, around the chest by suitable engaging means, such as complementary components 14 and 16 of a Velcro type fastener. Preferably, the smooth looped component 14 of the fastener is applied to the outside of the chest strap to minimize discomfort on contact with the affected arm. The smooth looped component 14 is extended at 14a well under the arm of the wearer, and a back anchor strip 18 is applied to the inside of the chest strap to extend across the back of the wearer and forward well under his or her arm. Preferably the front anchor portion 14a and the back anchor portion 18 overlap each other by several inches so that in some areas under the arm there are both front and back anchor looped portions for extra gripping.

A shoulder strap 20 is formed in two sections 22 and 24 so that they can be buckled together and adjusted at 26. The long section 22 of the shoulder strap is formed in a loop at one end 28 and has on the inside thereof a hooked or barbed fastener fabric 30 that grips and holds the hooked fabric 18 to fix the shoulder strap firmly in place. In applying the strap one may insert his fingers into the loop 28 to free it from the looped fabric 18, move the shoulder strap loop 28 to a desired location on the chest strap 12 and then press the loop 28 to fix the strap 22 firmly in place. At the other end or distal end of the shoulder strap 22 complementary smooth and barbed components 32 and 34 of a Velcro fastener are disposed in tandem so that the end of the strap may be inserted through the belt loop 26, folded back onto itself and fixed firmly in place.

The other, shorter section 24 of the shoulder strap 20 is also fixed in place by a barbed Velcro fastener component and carried on the shorter section 24, as by means of a belt loop 36 is a wrist strap 38 that has complementary strips of Velcro fastener fabric 40 and 42 disposed in tandem so that the wrist strap 38 may be brought up through the second strap buckles 44 and then folded back onto itself and secured firmly in place. Also carried on the chest strap 10 are upper arm restraint loops 46 and 48, which are slipped over the chest strap 12 and locked firmly in place on the smooth loop front anchor strip 14a by means of a complementary barbed fastener components on the inside of the loops 46 and 48. For complete immobility of the upper arm and shoulder, an arm restraint strap 50 is extended through both loops 46 and 48, buckled together at 52 and then folded over onto itself and attached by complementary fastener components 54 and 56 arranged in tandem.

Finally, to secure the lower arm in place an arm strap 58 is formed at one end in a loop 60, which is anchored in place on the front anchor strip 14a by means of a complementary fastener component inside the loop 60. Carried on the strap 58 is a buckle or belt loop 62 through which the other end of the arm strap is threaded, folded over onto itself and secured in place by complementary fastener components 64 and 66.

Certain stroke victims normally allow a shoulder to droop or sag. In such case, the shoulder strap 20 may be positioned over either shoulder, preferably the near shoulder if well. Then, the forearm strap 58 is wrapped around the arm and tightened to raise the elbow and bring the shoulders horizontal.

In operation to immobilize the right arm, the chest strap 12 is secured around the wearer in the position shown in FIG. 1 and complementary fastener components 14 and 16 are engaged to hold it firmly in place. The shoulder strap 20 is extended over the wearer, snugged up by extending the long length 22 through the belt loop 26 and fixed firmly in place by engagement of the fastener components 32 and 34. Then, the arm restraint strap 50, having been extended through loops 46 and 48 is wrapped around the upper arm of the wearer and snugged tight by engagement of the fastener components 54 and 56. In similar fashion, the lower arm strap 58 and the wrist strap 38 are wrapped around the lower arm and wrist of the wearer and fixed snugly in place. This completely immobilizes the arm and shoulder of the patient. In the event that some very little mobility of the shoulder is desired, the upper arm restraint strap 50 may be extended through only one of the loops 46 and 48 so that there is a little more play. In addition, the lower arm restraint strap 58 may be removed. If a greater amount of mobility is desired, the arm restraint strap 50 may be removed from the loops 46 and 48 and secured by means of a cord 68 (FIG. 5) which is tied through a ring or eye 70 carried on one of the loops 48.

In the event that it is desired to apply the appliance to the left arm and shoulder of the patient, the loops 24 of the wrist strap 38, 28 of the main shoulder strap 22 and 60 of the arm strap 58 are removed from the chest strap 12 and the chest strap is inverted from the position shown in FIG. 1 so that the arm restraint 50 is located to the right in FIG. 1 and the lower edge of the chest strap in FIG. 1 becomes the top edge. The loops 24, 28 and 60 may now be applied so that they will extend in the direction as strap 22 is shown in phantom in FIG. 1.

It will be noted that the shoulder strap 20, the wrist strap 38, the upper arm restraint strap 50 and the lower arm strap 58 may all be applied by the wearer by slipping the appropriate strap through a belt loop, pulling it as tightly as desired and then attaching it by engaging the complementary fastener components. In the event that the device is to be used by a tending person such as a paramedic, wrist and arm straps such as shown in FIG. 2 at 38 will suffice. There, the strap 38 is attached to the short segment 24 of the shoulder strap intermediate its ends so that a smooth loop component of the Velcro fastener is attached to one end and the barbed component 42a is sewn to the other end so that the two ends may be wrapped around the lower arm or wrist of the wearer, brought together and secured.

Figure 6:
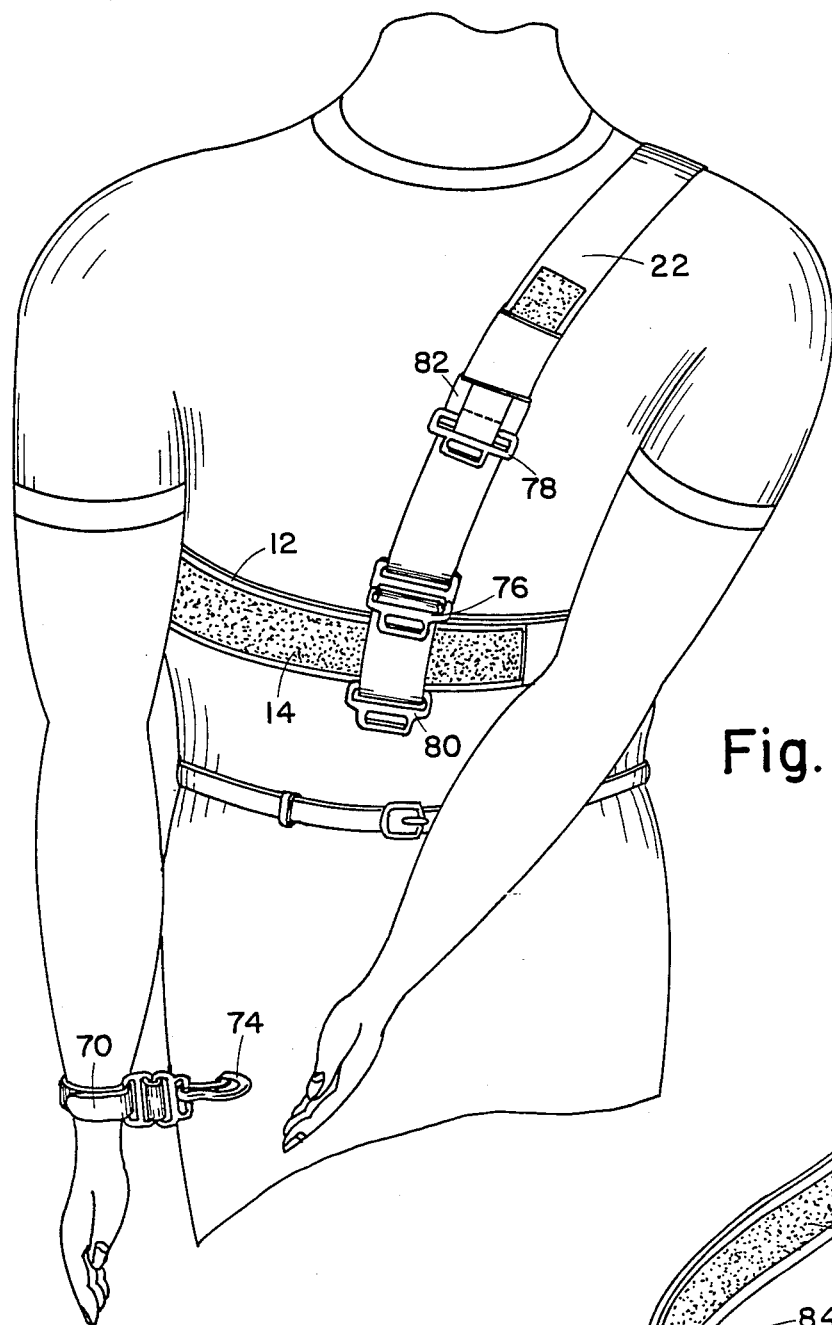
FIG. 6 is a view in perspective showing still another form of wrist strap and adjustable arm sling.

In some cases, as with a stroke, the patient is unable to raise his arm to the level of the chest strap 12 (FIGS. 3 and 6). In such case, the alternative wrist strap 70 may be employed. There, the strap 70 has secured at one end, a loop or eye 72 carrying a hook or clip 74 that hooks into an eye 76 carried on the short segment 24 of the shoulder strap. The wrist strap 70 is first applied to the wrist as shown in FIG. 6, and then the wrist is raised to the level of the eye 76 and hooked in place. Also as shown in FIG. 6 additional eyes 78 and 80 may be attached to the shoulder strap 22, as by means of small loops 82 carrying complementary Velcro component for attachment to the component 32 on the shoulder strap 22. In this way, the wrist may be shifted to different levels to improve comfort.

Figure 7:
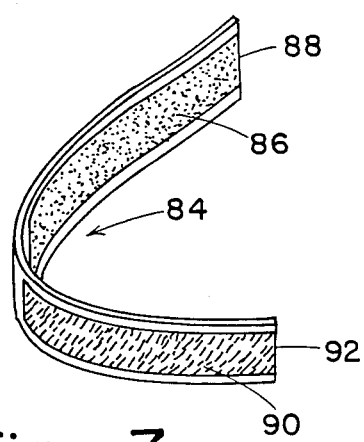
FIG. 7 is a view in perspective of a strap extension.

In some cases, one or more of the straps involved in this appliance have to be extended. For example, it may be desired to extend the chest strap 12 or the shoulder strap 22 for a larger person, or one may wish to lengthen a wrist strap 38 or 38a in order to accommodate a cast. In such case, the strap extension 84 is shown in FIG. 7. On the strap 84, a strip of a smooth loop fastener component 86 is sewn on one side of the strap 84 to extend from one end 88 toward the middle and a barbed strip is sewn to the other side to extend from the other end 92 toward the middle. For example, to extend the chest strap 12 shown in FIG. 1, the barbed component 90 is attached to the looped component 14 on the chest strap, extending the looped component 86 of the extension 84 to receive the barbed component 16 on the chest strap.

While this invention has been described in conjunction with preferred embodiments thereof, it is obvious that modifications and changes therein may be made by those skilled in the art to which it pertains, without departing from the spirit and scope of this invention, as defined by the claims appended hereto.

What is claimed as invention is:
1. An arm brace comprising:
a chest strap to be placed on and around the chest of the wearer so that the ends thereof overlap at the front;
interengageable size adjustment Velcro type fastening means on the ends of said chest strap;
a front anchor Velcro fastener first component strip secured to said chest strap to extend from the chest to under the arm of the wearer;
a back anchor Velcro type fastener first component strip secured to said chest strap along the mid-portion thereof to extend from under said arm across the back of the wearer;
a two-piece shoulder strap;
a long length of said shoulder strap being folded back at one end and secured to itself to form a back terminal loop to be received over said chest strap and moved to a selected position at the back of the wearer to engage said back anchor first component strip, there being a Velcro type fastener second component piece on the inside of said back terminal loop to lock said back loop in place;

a short length of said shoulder strap being folded back at one end and secured to itself to form a front terminal loop to be received over said chest strap and moved to a selected position in front of the wearer to engage said front anchor first component strip, there being a Velcro type fastener second component piece on the inside of said front terminal loop to lock said front loop in place;

a belt loop carried on said short length to receive said long length;

complementary Velcro type fastener components secured in tandem on the outer side of said long length from the other end thereof so that said long length can be brought over the wearer's shoulder, extended through said belt loop and then folded over onto itself with said complementary components in engagement and secured, enabling the wearer to adjust the effective length of said long length and secure said other end thereof; and a wrist strap secured to said short length and conditioned to be wrapped around a wrist of the wearer and secured.

2. The arm brace defined by claim 1 wherein:
said Velcro type fastener first component is relatively smooth with a multiplicity of small fabric loops; and
said Velcro type fastener second component has a multiplicity of small barbs or hooks.

3. The arm brace defined by claim 1 wherein:
said back anchor component strip is secured to the inside of said chest strap.

4. The arm brace defined by claim 1 wherein:
said wrist strap is secured at one end thereof to said short length and carries at said one end a wrist strap loop;
complementary Velcro type fastener strips secured in tandem on said wrist strap so that said wrist strap may be wrapped around the wrist of the wearer, extended through said wrist strap loop and secured onto itself.

5. The arm brace defined by claim 1 wherein:
said wrist strap is secured intermediate its ends to said short length;
complementary Velcro type fastener strips secured to extend from the ends of said wrist strap so that said wrist strap may be wrapped around the wrist of the wearer and the ends thereof secured together.

6. The arm brace defined by claim 1 including:
an eye carried on said shoulder strap; and
a complementary suspension hook carried on said wrist strap and engageable with said eye so that said wrist strap may be suspended from said shoulder strap after it is wrapped around the wrist.

7. The arm brace defined by claim 6 including:
an accessory band conditioned to be positioned selectively on said shoulder strap on the front of the wearer and secured in place by complementary Velcro fastener components; and
an eye carried on said accessory band to receive said suspension hook.

8. The arm brace defined by claim 1 including:
an extension strap to extend the length of one of said straps;
said extension strap having a Velcro type fastener first component strip on one side thereof extending from one end thereof and a Velcro fastener second component strip on the other side thereof extending from the other end thereof.

9. The arm brace defined by claim 1 including:
a first upper arm restraint loop secured to said chest strap to be positioned on the side of the wearer;
an arm restraint strap conditioned to be wrapped around the upper arm of the wearer and secured; and
means attaching said arm restraint strap to said first upper arm restraint loop.

10. The arm brace defined by claim 9 wherein:
said attaching means is a line extending between said first upper arm restraint loop and said arm restraint strap to limit movement of the upper arm of the wearer from the chest.

11. The arm brace defined by claim 9 wherein:
said arm restraint strap is attached to said upper arm restraint loop by being received therethrough.

12. The arm brace defined by claim 9 including:
a second upper arm restraint loop secured to said chest strap adjacent to but spaced from said first upper arm restraint loop;
said arm restraint strap being received through said first and second upper arm restraint loops.

13. The arm brace defined by claim 1 including:
a forearm restraint strap;
said forearm restraint strap being folded back at one end thereof and secured to itself to form an anchor loop to be received over said chest strap front anchor first component strip;
said forearm restraint strap anchor loop having a Velcro type fastener second component piece on the inside thereof so that said forearm restraint strap anchor loop may be received over said chest strap front anchor Velcro fastener and anchored to a selected position across the chest of the wearer;
a belt loop on said anchor loop; and
complementary Velcro type fastener component strips secured in tandem on the outer side of said forearm restraint strap so that said forearm restraint strap may be wrapped around the forearm of the wearer, extended through said belt loop and then folded over onto itself with said complementary fastener components in engagement.

14. An arm brace comprising:
a chest strap to be placed on and around the chest of the wearer so that the ends thereof overlap at the front;
interengageable size adjustment Velcro type fastening means on the ends of said chest strap;
a front anchor Velcro type fastener first component strip secured to said chest strap to extend from the chest to under the arm of the wearer;
a back anchor Velcro type fastener first component strip secured to said chest strap along the mid-portion thereof to extend from under said arm across the back of the wearer;
a two-piece shoulder strap;
a long length of said shoulder strap being folded back at one end and secured to itself to form a back terminal loop to be received over said chest strap and moved to a selected position at the back of the wearer to engage said back anchor first component strip, there being a Velcro type fastener second component piece on the inside of said back terminal loop;

a short length of said shoulder strap being folded back at one end and secured to itself to form a front terminal loop to be received over said chest strap to engage said front anchor first component strip, there being a Velcro type fastener second component piece on the inside of said front terminal loop;

a belt loop carried on said short length to receive said long length;

complementary Velcro type fastener components secured in tandem on the outer side of said long length from the other end thereof so that said long length can be brought over the wearer's shoulder, extended through said belt loop and then folded over onto itself with said complementary components in engagement and secured, enabling the wearer to adjust the effective length of said long length and secured said other end thereof;

a first upper arm restraint loop received on said chest strap to be positioned on the side of the wearer over said front anchor Velcro type first component strip;

said first upper arm restraint loop having Velcro type fasteners second component means on the inside thereof so that said restraint loop may be anchored in a selected position on said first component strip;

an upper arm restraint strap conditioned to be wrapped around the upper arm of the wearer and secured; and means attaching said upper arm restraint strap to said first upper arm restraint loop.

15. The arm brace defined by claim 14 wherein:
said attaching means is a line extending between said first upper arm restraint loop and said upper arm restraint strap to limit movement of the upper arm of the wearer from the chest.

16. The arm brace defined by claim 14 wherein:
said upper arm restraint strap is attached to said upper arm restraint loop by being received therethrough.

17. The arm brace defined by claim 14 including:
a second upper arm restraint loop received on said chest strap adjacent to but spaced from said first upper arm restraint loop;
said arm restraint strap being received through said first and second upper arm restraint loops.

18. The arm brace defined by claim 1 including:
a forearm restraint strap;
said forearm restraint strap being folded back at one end thereof and secured to itself to form an anchor loop to be received over said chest strap front anchor first component strip;
said forearm restraint strap anchor loop having a Velcro type fastener second component piece on the inside thereof so that said forearm restraint strap anchor loop may be received over said chest strap front anchor Velcro fastener and anchored to a selected position across the chest of the wearer;
a belt loop on said anchor loop; and
complementary Velcro type fastener component strips secured in tandem on the outer side of said forearm restraint strap so that said forearm restraint strap may be wrapped around the forearm of the wearer, extended through said belt loop and then folded over onto itself with said complementary fastener components in engagement.

19. The arm brace defined by claim 14 wherein:
said back anchor first component strip is secured to the inside of said chest strap.

20. The arm brace defined by claim 19 wherein:
said front anchor first component strip is secured to the outside of said chest strap and said front and back anchor first component strips are disposed in overlapping relationship.

21. A posture corrector comprising:
a chest strap to be placed on and around the chest of the wearer so that the ends thereof overlap at the front;
interengageable size adjustment Velcro type fastening means on the ends of said chest strap;
a front anchor Velcro fastener first component strip secured to said chest strap to extend from the chest to under the arm of the wearer;
a back anchor Velcro type fastener first component strip secured to said chest strap along the mid-portion thereof to extend from under said arm across the back of the wearer;
a two-piece shoulder strap;
a long length of said shoulder strap being folded back at one end and secured to itself to form a back terminal loop to be received over said chest strap and moved to be positioned at the back of the wearer to engage said back anchor first component strip, there being a Velcro type fastener second component piece on the inside of said back terminal loop;
a short length of said shoulder strap being folded back at one. end and secured to itself to form a front terminal loop to be received over said chest strap and moved to be positioned in front of the wearer to engage said front anchor first component strip, there being a Velcro type fastener second component piece on the inside of said front terminal loop;
a belt loop carried on said short length to receive said long length;
complementary Velcro type fastener components secured in tandem on the outer side of said long length from the other end thereof so that said long length can be brought over the wearer's shoulder, extended through said belt loop and then folded over onto itself with said complementary components in engagement and secured, enabling the wearer to adjust the effective length of said long length and secure said other end thereof;
a forearm restraint strap;
said forearm restraint strap being folded back at one end thereof and secured to itself to form an anchor loop to be received over said chest strap front anchor first component strip;
said forearm restraint strap anchor loop having a Velcro type fastener second component piece on the inside thereof so that said forearm restraint strap anchor loop may be received over said chest strap front anchor Velcro fastener and anchored to a selected position across the chest of the wearer;
a belt loop on said anchor loop; and
complementary Velcro type fastener component strips secured in tandem on the outer side of said forearm restraint strap so that said forearm restraint strap may be wrapped around the forearm of the wearer, extended through said belt loop and then folded over onto itself with said complementary fastener components in engagement.

* * * * *